United States Patent
Carry et al.

(10) Patent No.: US 9,221,817 B2
(45) Date of Patent: Dec. 29, 2015

(54) ANTI-CANCER COMPOUND AND PHARMACEUTICAL COMPOSITION CONTAINING THE SAME

(71) Applicant: SANOFI, Paris (FR)

(72) Inventors: Jean-Christophe Carry, Paris (FR); Michel Cheve, Paris (FR); Francois Clerc, Paris (FR); Cecile Combeau, Paris (FR); Sylvie Gontier, Paris (FR); Alain Krick, Paris (FR); Sylvette Lachaud, Paris (FR); Laurent Schio, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/728,846

(22) Filed: Jun. 2, 2015

(65) Prior Publication Data

US 2015/0266877 A1    Sep. 24, 2015

Related U.S. Application Data

(62) Division of application No. 13/320,965, filed as application No. PCT/FR2010/050948 on May 17, 2010, now Pat. No. 9,073,917.

(30) Foreign Application Priority Data

May 18, 2009  (FR) .................................... 0902392

(51) Int. Cl.
*A61K 31/4745* (2006.01)
*A61P 35/00* (2006.01)
*C07D 405/12* (2006.01)
*C07D 471/04* (2006.01)

(52) U.S. Cl.
CPC .................................. *C07D 471/04* (2013.01)

(58) Field of Classification Search
USPC .............................................. 514/292; 546/84
See application file for complete search history.

(56) References Cited

U.S. PATENT DOCUMENTS 9,073,917 B2    7/2015   Carry et al.

FOREIGN PATENT DOCUMENTS

WO   WO-2007/012972 A2   2/2007
WO   WO-2007/012972 A3   2/2007

OTHER PUBLICATIONS

Coumar, Mohane Selvaraj et al., "Advances in Aurora kinase inhibitor patents," Expert Opinion on Therapeutic Patents (2009), vol. 19, pp. 321-356.
International Search Report dated Sep. 13, 2010 issued in PCT/FR2010/050948.
Troy Voelker. et al., o-Nitrobenzyl as a Phoyocleavable Nitrogen Protecting Group for Indoles, Benzimidazole, and 6-Chlorouracil, Tetrahedron letters, (1998), vol. 39, pp. 359-362.
Yuhpyng L. Chen, Vinyl Protecting Group for Benzimidazole Nitrogen: Synthesis of Benzimidazole-Penam Alcohol, Tetrahedron letters, (1989), vol. 30, No. 9, pp. 1067-1068.

*Primary Examiner* — Kathrien Cruz
(74) *Attorney, Agent, or Firm* — Morrison & Foerster LLP

(57) ABSTRACT

The invention relates to a compound of formula (I), more specifically in the levorotatory form (1a) thereof, in particular the form having a rotatory power $[\alpha]D=-38.6+0.7$ at a concentration of 0.698 mg/ml in methanol. The compound may be in the form of a base or an acid addition salt, in particular a pharmaceutically acceptable acid. The compound is a selective Aurora A and B kinase inhibitor and can be used as an anticancer drug.

5 Claims, No Drawings

ANTI-CANCER COMPOUND AND PHARMACEUTICAL COMPOSITION CONTAINING THE SAME

CROSS-REFERENCE TO RELATED APPLICATIONS

This application is a divisional of U.S. patent application Ser. No. 13/320,965, which adopts the international filing date of May 17, 2010, which is a National Phase application under 35 U.S.C. §371 of International Application No. PCT/FR2010/050948 filed May 17, 2010, and claims the benefit of priority of French Application No. 0902392 filed May 18, 2009, the disclosures of each of which are incorporated herein by reference in their entirety.

The present invention relates to the compound of formula (I):

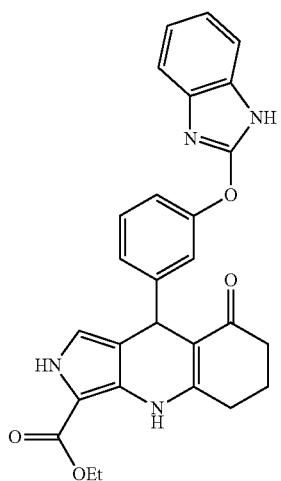

(I)

and to the pharmaceutical composition comprising it. This compound is preferably the levogyratory compound (Ia). This compound can be used as an anti-cancer ingredient. The invention also relates to a process for preparing the compound (I) or (Ia) and also to some of the intermediates in said process.

TECHNICAL PROBLEM

A number of cancer treatment strategies are aimed at inhibiting the Aurora-type kinases, particularly Aurora A and B, which are involved in the regulation of mitosis; in this regard, see *Nature Reviews* 2004, 4, 927-936; *Cancer Res.* 2002, 94, 1320; *Oncogene* 2002, 21, 6175; *Mol. Cell. Biol.* 2009, 29(4), 1059-1071; *Expert Opin. Ther. Patents* 2005, 15(9), 1169-1182; *Clin. Cancer Res.* 2008, 14(6), 1639.

Some Aurora inhibitor compounds (for example, MLN-8237 from Millennium, AZD-1152 from Astra-Zeneca or SNS-314 from Sunesis) are presently under evaluation in clinical trials. MLN-8237 is selective for Aurora A while AZD-1152 is selective for Aurora B. Since both kinases, Aurora A and B, are deregulated in cancer, inhibiting both Aurora A and B provides an advantage relative to selective inhibition of one kinase or the other. Moreover, multikinase compounds are in existence, such as the compound AT-9283 from Astex, which inhibit a number of kinases, including Aurora A and B. For this type of compound it is difficult to predict that the inhibition of the Aurora kinases might actually be exploited clinically, since the inhibition of kinases other than Aurora A and B is likely to give rise to side effects. One technical problem the invention intends to solve is therefore that of developing a compound which is a potent and selective inhibitor of Aurora A and B.

The cyclic nucleotide phosphodiesterase enzyme PDE3 plays a major part in the signalling mediated by the cyclic nucleotides cAMP and cGMP that takes place in the myocytes of the smooth cardiac and vascular muscles. The inhibition of PDE3 by small molecules has an inotropic and vasodilatory action, which may prove to be useful on a short-term basis for the treatment of certain cardiomyopathies in which defects in cardiac contraction are a feature. It has been shown, however, that the long-term use of these molecules increases mortality among this type of patient. Furthermore, the use of PDE3 inhibitors in patients who do not present this type of pathology, such as patients affected by cancer, may give rise to unwanted effects on cardiac rhythm. It is therefore important, in the context of an anti-cancer therapy, not to inhibit PDE3. In this regard, see *Exp. Opin. Invest. drugs* 2002, 11, 1529-1536 "Inhibitors of PDE3 as adjunct therapy for dilated cardiomyopathy"; *Eur. Heart J. supplements* 2002, 4 (supplement D), D43-D49 "What is wrong with positive inotropic drugs? Lessons from basic science and clinical trials". Another technical problem the invention intends to solve is that the Aurora A and B inhibitor compound shall not inhibit the enzyme PDE3.

It is also important that the anti-cancer ingredient presents a metabolic stability (see section 10.2.2 of "Chimie pharmaceutique" G. L. Patrick, De Boeck, published 2003, ISBN=2-7445-0154-9). The reason is that the inadequacy of the pharmacokinetics of pharmaceutical compounds is one of the primary reasons for failure in their development (*Curr. Pharm.* 2005, 11, 3545 "Why drugs fail—a study on side effects in new chemical entities"). Moreover, the metabolism is often a major determinant of clearance, of drug interactions, of intra-individual variability in pharmacokinetics, and of clinical efficacy and toxicity (*Curr. Drug Metal*). 2004, 5(5), 443-462 "Human hepatocytes in primary culture: the choice to investigate drug metabolism in man"). Another technical problem the invention intends to solve is that the Aurora A and B inhibitor compound shall exhibit high chemical and metabolic stability.

PRIOR ART

Bioorg. Med. Chem. Lett. 2002, 12, 1481-1484 describes in table II the compound 6A, which has a different tricyclic structure.

WO 01/36422 describes compounds having a different tricyclic structure.

WO 2004/005323 describes the compound E5A29 of formula (a):

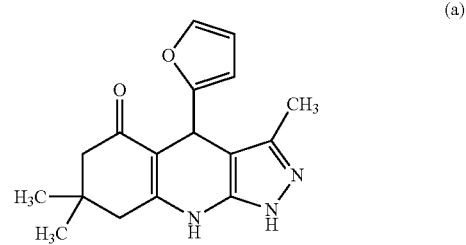 [SMILES: Cc1n[nH]c2c1C(c1ccco1)C1=C(CC(C)(C)CC1=O)N2]

(a)

as an EPO receptor having a different tricyclic structure. Furthermore, the compound does not include a phenyl ring substituted by the group —O-benzimidazolyl at the top of the tricyclic ring system.

WO 2005/016245 describes anti-cancer compounds having a different tricyclic structure, of formula (b):

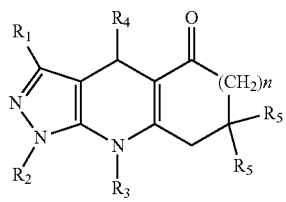

in which $R_4$ may represent a substituted phenyl group. Substitution by the —O-benzimidazolyl group is neither described nor suggested, WO 2007/012972 and EP 1746097 describe anti-cancer compounds of formula (c)

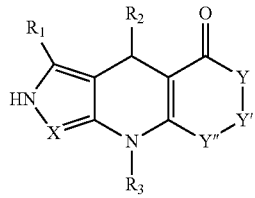

and, in one embodiment, of the formula (c'):

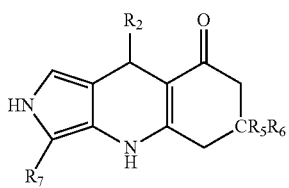

$R_2$ represents a substituted aryl or heteroaryl group. X represents N or $CR_7$, $R_5$ and $R_6$ may both represent H or $CH_3$. No example in WO 2007/012972 contains the group

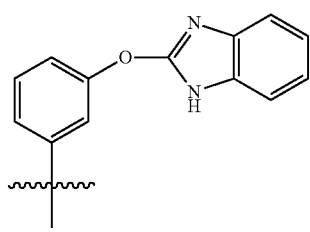 [SMILES: *c1cccc(Oc2nc3ccccc3[nH]2)c1]

which characterizes the compound of formula (I). Moreover, among the compounds resolved. WO 2007/012972 teaches that it is dextrogyratory compounds which are the most active on Aurora A or B (cf. ex. 119 and 120 in the table on page 147).

WO 02/062795 describes compounds of formula (d):

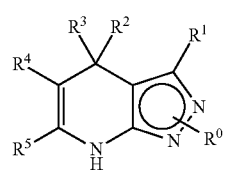

in which $R_4$ and $R_5$ may optionally form a 5- or 6-membered ring.

BRIEF DESCRIPTION OF THE INVENTION

The invention relates to the compound of formula (I):

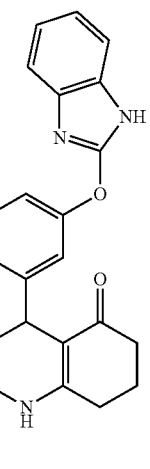

more particularly in its levogyratory form (Ia), particularly that exhibiting the optical rotation $[\alpha]_D=-38.6\pm0.7$ at a concentration of 0.698 mg/ml in methanol. The compound may exist in the form of a base or an addition salt with an acid, particularly a pharmaceutically acceptable acid. This compound is a selective inhibitor of Aurora A and B kinases. It can be used as an anti-cancer ingredient.

The invention also relates to a pharmaceutical composition comprising the compound and at least one pharmaceutically acceptable excipient, and to the medicament comprising the compound.

The invention also relates to the process for preparing the compound, comprising;

reacting together the three compounds below. PG denoting a protective group for the NH function of the benzimidazole

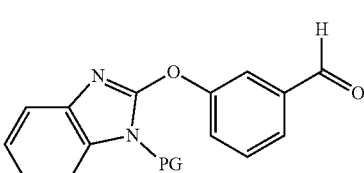

-continued

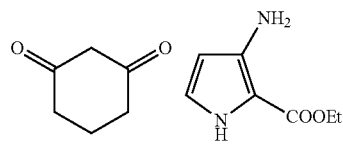

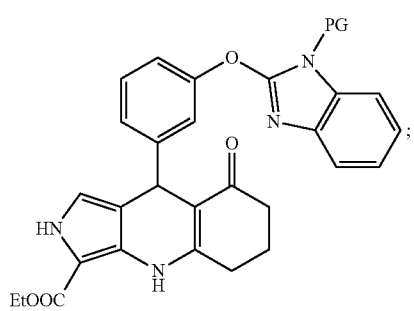

to give the compound:

deprotecting the NH function of benzimidazole, to give the compound of formula (I);

where appropriate, isolating the levogyratory compound.

The reaction between the three compounds is carried out in an alcohol at reflux, particularly 1-butanol. The following intermediates also form part of the invention:

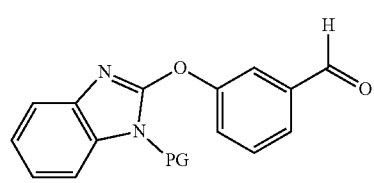

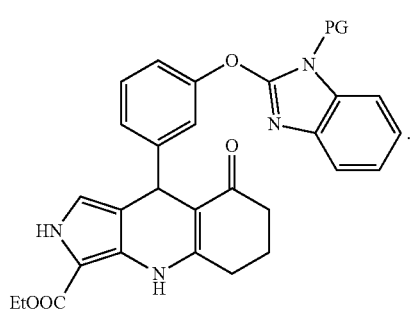

PG may be, for example, the group

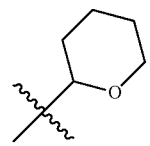 [SMILES: *C1CCCCO1]

DESCRIPTION OF THE INVENTION

The invention relates to the compound of formula (I):

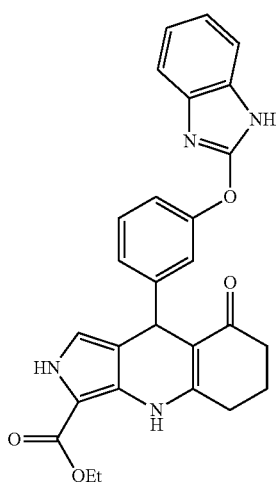

(I)

This compound may exist in a racemic form or in the form of the two levogyratory (Ia) and dextrogyratory (Ib) enantiomers. The levogyratory compound (Ia) has a selective inhibitory activity on Aurora A and B kinases which is much greater than that of the dextrogyratory enantiomer (Ib). The levogyratory compound (Ia) also has an anti-proliferative activity which is greater than that of the dextrogyratory enantiomer (Ib) (see Table I).

The three compounds (I), (Ia) and (Ib) may exist in the form of a base or an addition salt of an acid. The salt is advantageously prepared with a pharmaceutically acceptable acid (see P. Stahl, C. Wermuth; Handbook of Pharmaceutical Salts; Wiley Ed. ISBN-13: 978-3906390260, ISBN-10: 3906390268), although the salt of any other type of acid, which may be used, for example, for a purification or isolation step, also forms part of the invention.

The compounds (I) and (Ia) may be used as anti-cancer ingredients or for preparing a medicament for treating a cancer. The cancer is more particularly a cancer in which Aurora A and/or B kinase(s) are/is involved.

The compounds (I), (Ia) and (Ib) are obtained according to Scheme I below:

Scheme I

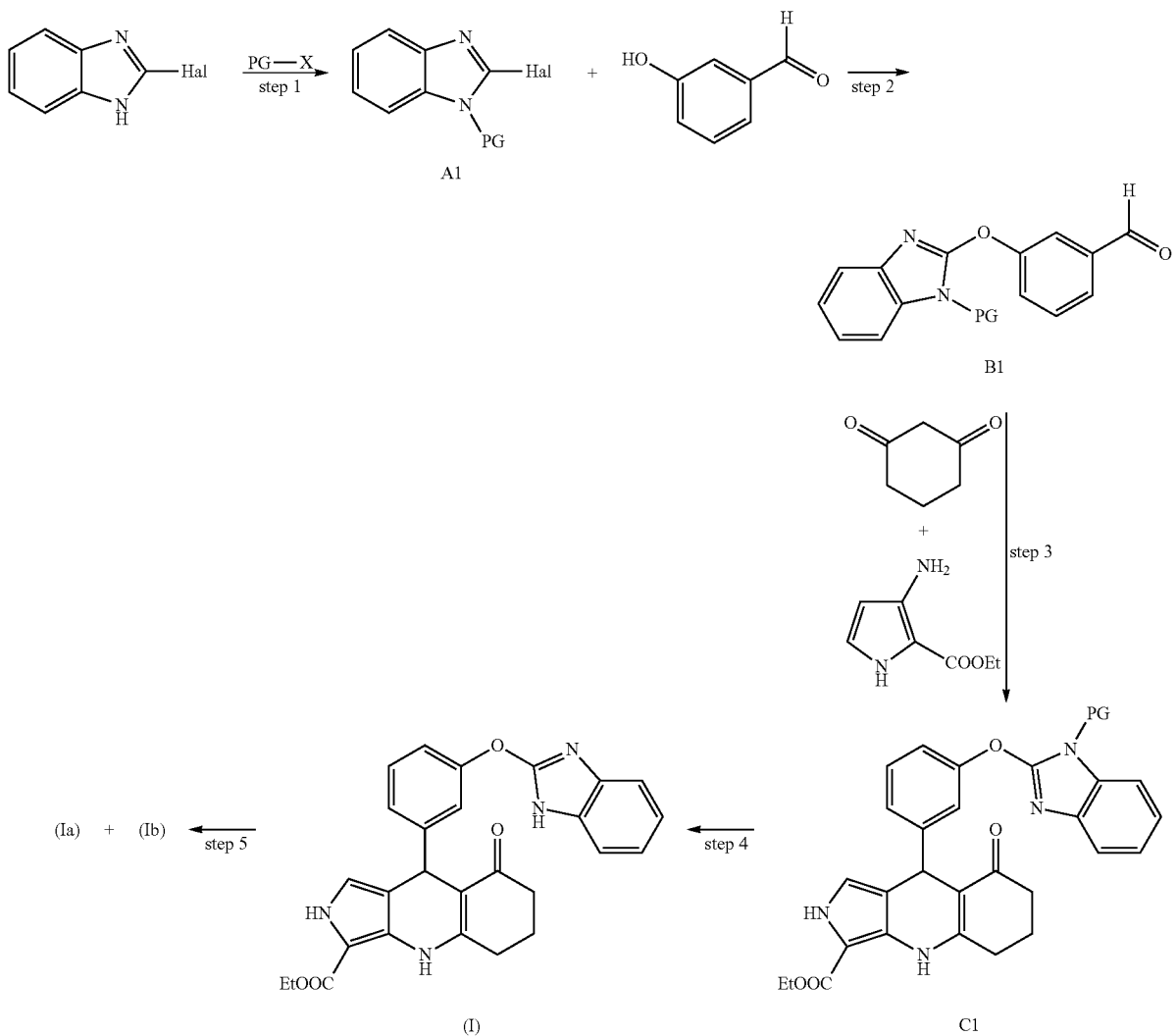

step 1: the NH function of a 2-halo-benzimidazole (Hal=Br or Cl) is protected using a protective group PG, to give A1. PG-X represents a reagent which introduces the protective group PG. PG may be, more particularly, dihydropyran

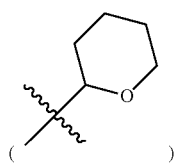 [SMILES: *C1CCCCO1]

and, in that case. PG-X represents 3,4-dihydro-2H-pyran

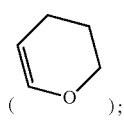

step 2: A1 is reacted with 3-formyl-phenol in the presence of a base producing the corresponding phenolate ion, to give B1. The base may be an alkali metal hydride, such as NaH, for example. The reaction is carried out in a polar aprotic solvent such as DMF;

step 3: B1, 3-amino-2-ethoxycarbonylpyrrole and 1,3-cyclohexanedione are reacted with one another, for example in an alcohol (e.g. 1-butanol) at reflux, to give C1;

step 4: the NH function of C1 is deprotected, to give the compound (I). The deprotection conditions are dependent on the nature of PG. For example, where PG represents dihydropyran, a strong acid is used;

step 5: using, for example, a chiral chromatography, the two enantiomers (Ia) and (Ib) are isolated.

For each of steps 1-5, reference may be made to the specific conditions described in example 1.

EXAMPLES

Analytical Methods

Method LC/MS-A

The products for analysis are separated on an Acquity Beh 018 UPLC column, 1.7 μm 2.1×50 mm (Waters) thermostated at 70° C. and eluted at a flow rate of 1 ml/min with a gradient from acetonitrile containing 0.1% formic acid (solvent B) into water containing 0.1% formic acid (solvent A); elution programmeme: isocratic stage at 5% of solvent B for 0.15 min, gradient from 5% to 100% of solvent B in 3.15 min then return to the initial conditions over 0.1 min. The products are detected by an Acquity PDA diode-array UV/vis detector (Waters, wavelength range scanned: 192-400 nm), a Sedex 85 light scattering detector (Sedere, nebulizing gas: nitrogen, nebulizing temperature: 32° C., nebulizing pressure 3.8 bar) and an Acquity SQD mass spectrometer (Waters, operating in positive and negative mode, mass range scanned: 80 to 800 amu).

Method LC/MS-B

The spectra were obtained on a Waters UPLC-SQD instrument in positive and/or negative electrospray ionization mode (ES+/−), under the following liquid chromatography conditions: column: ACQUITY BEH C18 1.7 μm, 2.1×50 mm; $T_{column}$: 50° C.; flow rate: 1 ml/min; solvents: A: $H_2O$ (01% formic acid); B: $CH_3CN$ (0.1% formic acid); gradient (2 min): 5% to 50% B in 0.8 min; 1.2 min: 100% B; 1.85 min 100% B; 1.95 min 5% B.

$^1H$ NMR

The spectra are recorded on a Bruker spectrometer, the product being dissolved in DMSO-d6. The chemical shifts 5 are expressed in ppm.

IR

The infrared spectrum is recorded on a Nicolet Nexus spectrometer, on a KBr disc, with a resolution of 2 $cm^{-1}$.

Measurement of the Optical Rotation

The optical rotations were recorded on a Perkin-Elmer 341 polarimeter.

Elemental Analysis

The elemental analyses were made on a Thermo EA1108 analyser.

Measurement of the Activity on Aurora A and B

The capacity to inhibit the kinase activity of the enzyme is estimated by measuring the residual kinase activity of the enzyme in the presence of different concentrations of the test compound (generally from 0.17 to 10 000 nM). A dose-response curve is produced, which allows an $IC_{50}$ (50% inhibitory concentration) to be determined. The kinase activity is measured by a radioactive assay of the amount of radioactive phosphate (33P) incorporated into a fragment of the protein NuMA (Nuclear Mitotic Apparatus protein) after 30 minutes of incubation at 37° C. The test compound is first dissolved at different concentrations in dimethyl sulphoxide (DMSO). Reaction takes place in the wells of a FlashPlate microtiter plate (Nickel Chelate FlashPlate-96, PerkinElmer). Each well (100 μl) contains 10 nM Aurora A, 500 nM NuMA, 1 μM ATP and 0.2 μCi ATP-γ-33P in a buffer of 50 mM Tris-HCl, pH=7.5; 10 mM $MgCl_2$; 50 mM NaCl, 1 mM dithiothreitol. The final percentage of DMSO is 3%. After homogenization by stirring, the plate is incubated at 37° C. for 30 minutes. The contents of the wells are then removed and the wells are washed with PBS buffer. The radioactivity is than measured using a TRILUX 1450 Microbeta counter (WALLAC). In each plate, there are eight control wells: four positive controls (maximum kinase activity), for which measurement is made in the presence of enzyme and substrate and in the absence of compound of the invention, and four negative controls (background) for which measurement is made in the absence of enzyme, substrate and test compound. The measurements are given in Table I.

Aurora A

The recombinant human enzyme Aurora A used is expressed in entire form with a poly-Histidine tag in N-terminal position and is produced in E. coli. A fragment (amino acids 1701-2115) of the human protein NuMA, with a poly-Histidine tag in C-terminal position, is expressed in recombinant form in E. coli.

Aurora B/Incenp

The entire human enzyme Aurora B is coexpressed with a fragment of the human protein Incenp (aa 821-918) in a baculovirus system and is expressed in insect cells. Aurora B has a poly-Histidine tag in N-terminal position, while the Incenp fragment possesses a Glutathione-S-Transferase (GST) tag in N-terminal position. The two proteins form a complex which is called Aurora B/Incenp. A fragment (aa1701-2115) of the human protein NuMA with a poly-Histidine tag in C-terminal position is expressed in recombinant form in E. coli. This fragment is used as substrate.

Measurement of the Cell Proliferation

Cells (tumour cell line HeLa-ref.: ATCC CCL-2 and HCT116 ref.: ATCC CCL-247) are contacted with the test compound for 96 hours, with $^{14}C$-thymidine added during the last 24 hours. The cell proliferation is estimated by the amount of $^{14}C$-thymidine incorporated in the cells.

The test compound is dissolved to form a stock solution at 10 mM in DMSO, and this stock solution is used to produce a range of serial dilutions, generally from 10 000 μM to 0.3 μM, these serial dilutions being themselves diluted 1/50 in the cell culture medium (20× solution) which will be used for 1/20 dilution in the cell culture plates. The final concentrations of the test compound will generally be between 10 000 and 0.3 nM.

D0: the cells are seeded in 96-well Cytostar plates in 180 μL of culture medium. The plates are then placed in an incubator at 37° C., 5% $CO_2$ for four hours. The test products are then added in a volume of 10 μL per well, starting from a 20× solution. This solution contains 2% of DMSO in the culture medium. The final concentration of DMSO is therefore 0.1%. The plates are then placed in an incubator at 37° C./5% $CO_2$ for 72 hours.

D3: after 72 hours, 10 μL per well of $^{14}C$-thymidine at 10 μCi/mL in the culture medium are added. The plates are then placed in an incubator at 37° C., 5% $CO_2$ for 24 hours.

D4: The incorporation of $^{14}C$ thymidine is measured on a Micro-Beta radioactivity counter (Perkin-Elmer) after this 24-hour, "pulse" period. The total time of treatment of the cells with the test product is 96 hours.

The percentage inhibitions IC50 are calculated in Excel using the following formula:

$$1\% \text{ Inhibition} = 100 * \left(1 - \left(\frac{X - \text{Blank}}{CC - \text{Blank}}\right)\right)$$

X=Measurement for the sample
CC=Cell Control
Blank=Measurement in the wells without cells $IC_{50}$ is calculated using the XLfit software (IDBS, UK) with the aid of formula 205, with the parameter D (Hill number) locked to a value of 1. The results are given in Table I.

Evaluation of the Effect of the Compounds of the Invention on the Activity of the Enzyme PDE3

The effect of the compounds of the invention on the activity of the enzyme PDE3 was evaluated by the company CEREP (Le bois l'Evêque, 86600 Celle l'Evescault, France; http://www.cerep.fr) in accordance with its standard protocol (see Bender, A. T., Beavo, J. A. *Pharmacol Rev.* 2006, 58, 488-520: the enzyme PDE3A in recombinant form is expressed in Sf9 cells, the substrate is cAMP and the residual AMPc is measured by HTRF. The reference inhibitor in the test is milrinone, whose $IC_{50}$ is 270 nM. The residual activity % are related to the control without inhibitor). The results are expressed either as the concentration which induces inhibition by 50% ($IC_{50}$) or as a percentage inhibition measured at a set concentration of the compound. The results are given in Table I.

Measurement of the Chemical Stability of the Compounds

The chemical stability of the compounds was measured in various media: 0.05 N hydrochloric acid in a 50/50 (v/v) water/acetonitrile mixture; 0.05 N sodium hydroxide in a 50/50 (v/v) water/acetonitrile mixture; sodium phosphate buffer, 25 mM, pH=7.4, in a 50/50 (v/v) water/acetonitrile mixture; sodium phosphate buffer 25 mM, pH=7.4, in a 50/50 (v/v) water/acetonitrile mixture containing 1% (w/v) of benzylamine hydrochloride; sodium phosphate buffer, 25 mM, pH=7.4 in a 50/50 (v/v) water/acetonitrile mixture containing 1% (v/v) of 2-mercaptoethanol. The compounds are diluted in the media under study at a final concentration of 100 µM, by dilution of a 10 mM stock solution in DMSO. The solutions are stored at 20° C. for a total time of 48 hours, and the concentration of the compounds under study is measured over time (t=0, 1, 6, 12, 24 and 48 hours) by HPLC. HPLC analysis is carried out with an Agilent system 1100 instrument equipped with a diode array detector on a Luna O18 column, 30×4.6 mm, 3 µm (Phenomenex) which is eluted with a gradient from acetonitrile (solvent B) into water containing 0.5% (v/v) of formic acid (solvent A) at a flow rate of 1.5 ml/min and a temperature of 25° C. The elution programme consists of a gradient from 10 to 90% solvent B in 5 minutes, followed by an isocratic stage of one minute at 90% of solvent B, and return to the initial conditions over one minute. The concentration of the products under study is estimated from the height and area of the characteristic peak of the product under study on a chromatogram at the maximum wavelength of each product. The area and the height measured at each time of sampling are related to the area and height obtained for the sample at time 0. When degradation is observed, a half-life is measured from the resulting time-concentration curve. The results are given in Table II.

Evaluation of the Metabolism in the Presence of Microsomal Preparations of Human and Murine Livers.

Whereas microsome preparations remain important in determining the metabolic stability of a pharmaceutical compound, primary hepatocyte culture allows a more detailed evaluation of its intrinsic clearance, and better vitro-vivo correlations suggest hepatic clearance in humans.

The compounds of the invention (5 µM) are incubated at physiological temperature over human and murine microsomal liver fractions (1 mg/ml of proteins), diluted in a phosphate buffer, in the presence of bovine serum albumin (1 mg/ml BSA), and the reduced form of nicotinamide adenine dinucleotide phosphate (1 mM NADPH). To terminate incubation, four volumes of acetonitrile containing corticosterone as internal standard (IS) are added. The samples are centrifuged and the supernatants are analysed by liquid chromatography/tandem mass spectrometry coupling (LC/MS-MS). The LC/MS-MS analysis is performed on a QTRAP API4000 mass spectrometer (Sciex) equipped with an 1100 series chromatography system (Agilent) and a Pal CTC automatic injector. The data are acquired and analysed using Analyst 1.4.1 software. The samples are separated on a 3 µm C18 Polaris column, eluted at a flow rate of 0.7 ml/min with a gradient from acetonitrile (solvent B) into water containing 0.1% formic acid (solvent A). The elution programme is composed of the gradient from 20 to 90% of solvent B in 2 minutes, an isocratic stage at 90% of solvent B, for 0.9 minute, and a return to the initial conditions in 0.1 minute. The area of the chromatographic peaks for the compound and for the internal standard are integrated using the Analyst-Classic algorithm. The metabolic stability of the products of the invention is estimated by comparing the integration ratios (ion currents of the compounds/ion current IS) measured after 0 minute (t0) and 20 minutes (t20) of incubation. The metabolic stability is then expressed as a percentage disappearance in accordance with the following formula:

$$\text{Metabolism \%} = (\text{ratio of peaks at } t0 - \text{ratio of peaks at } t20)/\text{ratio of peaks at } t0$$

The results are given in Table III.

Evaluation of the Clearance in the Presence of Human Hepatocytes.

The compounds of the invention (0.5 or 5 µM) are incubated for 24 hours in 48-well plates covered with collagen in the presence of fresh or cryopreserved human hepatocytes (~200 000 cells/well) obtained from specific donors, in an incubator at a physiological temperature. The incubations are carried out with a culture medium (HAM F12 William E). At various times (0; 0.5; 1; 2; 4; 6; 8 and 24 hours), 100 µl are sampled from each well, and the kinetics are halted by addition of 700 µl of a 70/30 (v/v) acetonitrile/water mixture containing corticosterone as internal standard (IS). The cells are then dissociated and the intracellular and extracellular media are mixed and stored in frozen form at −20° C. prior to their analysis. Following thawing, the samples are centrifuged at 300 g for 20 minutes and the supernatants are analysed by liquid chromatography/tandem mass spectrometry coupling (LC/MS-MS). The LC/MS-MS analysis is performed on a QTRAP API4000 mass spectrometer (Sciex) equipped with an 1100 series chromatography system (Agilent) and a Pal CTC automatic injector. The data are acquired and analysed using Analyst 1.4.1 software. The samples are separated on a 3 µm C18 Polaris column, eluted at a flow rate of 0.7 ml/min with a gradient from acetonitrile (solvent B) into water containing 0.1% formic acid (solvent A). The elution programme is composed of the gradient from 20 to 90% of solvent B in 2 minutes, an isocratic stage at 90% of solvent B, for 0.9 minute, and a return to the initial conditions in 0.1 minute. The concentration of the products of the invention is measured by integrating the ion current of the characteristic ions of the products, relative to the internal standard (IS). The compound/IS ratios obtained are related to calibration standards of known concentrations, thereby allowing the concentration of the products of the invention to be ascertained. The intrinsic clearance (expressed in $ml \cdot h^{-1} \cdot 10^{-6}$ cells) is then determined from the kinetic profiles (concentration/time), using the WinNonLin software (5.0). The results are given in Table IV.

Example 1
Preparation of ethyl 8-oxo-9-[3-(1H-benzimidazol-2-yloxy)phenyl]-4,5,6,7,8,9-hexahydro-2H-pyrrolo[3,4-b]quinoline-3-carboxylate (I)
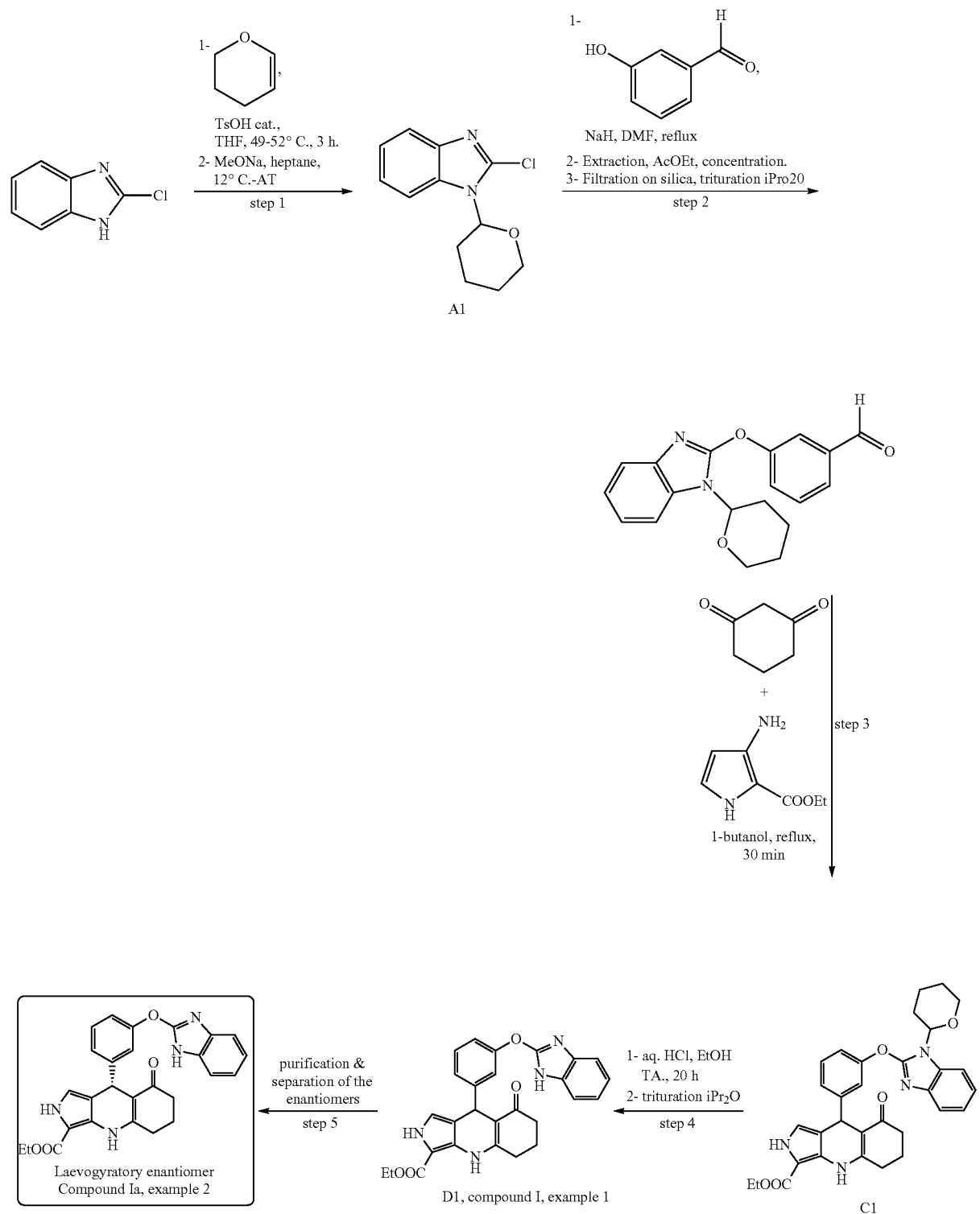

A1. 2-Chloro-1-(tetrahydro-pyran-2-yl)-1H-benzimidazole (CAS No. 208398-29-2)

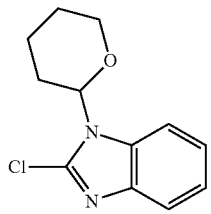 [SMILES: Clc1nc2ccccc2n1C1CCCCO1]

A 10 l reactor is charged, under argon and with stirring, with 2.5 l of THF, 180 g of 2-chlorobenzimidazole (1.18 mol) and 325 ml of 3,4-dihydro-2H-pyran (6.56 mol, 3 eq.). The reactor is heated until dissolution occurs (temperature of the mixture: 40° C.). Then 6.3 g of para-toluenesulphonic acid (0.033 mol, 0.028 eq.) are introduced. The temperature is held at between 49 and 52° C. for 2.5 h. Cooling takes place at 12° C. and 7.65 g of sodium methoxide (0.142 mol, 0.12 eq.) are added, with stirring maintained for a total time of 15 min. The temperature is then taken to 18° C., 5 l of n-heptane are added, and the whole mixture is filtered on 300 g of Clarcel FLO-M, the retentate being washed with 5 l of n-heptane. The filtrate is concentrated to dryness under reduced pressure to give 292.6 g of 2-chloro-1-(tetrahydro-pyran-2-yl)-1H-benzimidazole in the form of a slightly yellow oil (quantitative yield). $^1$H NMR (400 MHz, DMSO-d6): 1.42 to 2.01 (m, 5H); 2.21 to 2.34 (m, 1H); 3.69 to 3.78 (m, 1H); 4.12 (d, J=11.4 Hz, 1H); 5.72 (dd, J=2.4 and 11.2 Hz, 1H); 7.22 to 7.34 (m, 2H); 7.82 (d. J=72 Hz, 1H); 7.78 (d, J=7.2 Hz, 1H).

B1: 3-[1-(Tetrahydro-pyran-2-yl)-1H-benzimidazol-2-yloxy]benzaldehyde

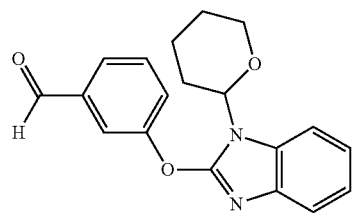 [SMILES: O=Cc1cccc(Oc2nc3ccccc3n2C2CCCCO2)c1]

Two 2 l three-necked round-bottomed flasks, each equipped with a condenser, a thermometer and a stirrer shaft, are charged under argon with N,N-dimethylformamide (0.4 l per flask), and 3-hydroxybenzaldehyde (68.5 g, flask 1; 64.2 g, flask 2; 1.08 mol). Sodium hydride (60% dispersion in mineral oil) is then added in portions (flask 1: 26 g; flask 2; 24 g; 1.25 mol, 1.2 eq.), the maximum temperature during the addition being 32° C. 2-chloro-1-(tetrahydro-pyran-2-yl)-1H-benzimidazole (A1), purity estimated at 85%) is then introduced (flask 1: 151 g in 0.5 l of N,N-dimethylformamide; flask 2: 142 g in 0.5 l of N,N-dimethylformamide; 1.05 mol, 0.97 eq.). The mixture is than heated at reflux (temperature 140° C., temperature rise time 40 min) and the reflux is maintained for 1 h. Heating is then stopped and the mixture is allowed to cool over 1.5 h. The contents of the two flasks are combined. The combined mixture is mixed slowly into 5 l of ice-water. The aqueous phase obtained is then extracted with 4×2.5 l of ethyl acetate (AcOEt). The organic phases are then combined, washed with 3 l of water and then with 2 l of saturated NaCl solution, and finally dried by addition of MgSO$_4$ overnight. The organic phase obtained is then filtered on a glass frit (porosity 4) and concentrated to dryness under reduced pressure to give 385 g of a brown oil (LC/MS-A, tr (retention time)=1.86 min, MS positive mode: m/z=323.16).

A fraction of 158 g of the crude product obtained above is dissolved hot in 1.5 l of an n-heptane/AcOEt mixture (8/2 by volume), combined with 500 g of silica (70-30 mesh), and the mixture is stirred for 45 min. The resulting suspension is filtered on Celite, and washed with 3 l of an n-heptane/AcOEt mixture (8/2 by volume). The organic phase obtained is concentrated to dryness under reduced pressure. The residue is resuspended in 200 ml of isopropyl ether by mechanical stirring and ultrasound treatment, and then filtered on a glass frit (porosity 3). The resulting solid is washed with 2×40 ml of isopropyl ether and dried under reduced pressure at 40° C. for 16 h to give 68 g of solid. A similar treatment applied to the remainder of the crude product produces 87.8 g of solid. The solids obtained are combined and homogenized to give 155.8 g of 3-[1-(tetrahydro-pyran-2-yl)-1H-benzimidazol-2-yloxy]benzaldehyde in the form of pale beige crystals (LC/MS-A, tr=1.87 min. MS positive mode m/z=323.13). MS (LC/MS-B): tr=1.00 min; [M+H]+: m/z 323; $^1$H NMR (400 MHz, DMSO-d6): 1.54 to 1.82 (m, 1H); 1.63 to 1.84 (m, 2H); 1.92 to 2.03 (m, 2H); 2.30 to 2.42 (m, 1H); 3.70 to 3.79 (m, 1H); 410 (d, J=11.5 Hz, 1H); 5.74 (dd, J=2.1 and 11.1 Hz, 1H); 7.13 to 7.22 (m, 2H); 7.43 (d, J=7.3 Hz, 1H); 7.65 (d, J=7.3 Hz, 1H); 7.73 (t, J=7.8 Hz, 1H); 7.78 to 7.83 (m, 1H); 7.87 (d, J=7.8 Hz, 1H); 7.96 (s, 1H); 10.05 (s, 1H).

Washing of the silica phases used above with 2 l of an n-heptane/AcOEt mixture (1/1 by volume) produces 67 g of product following concentration to dryness under reduced pressure. This product is taken up in 2 l of an n-heptane/AcOEt mixture (9/1 by volume), combined with 285 g of silica (70-30 mesh), stirred and treated with ultrasound for 1 h. The suspension is then filtered on Celite and the solid phase is washed with 2 l of an n-heptane/AcOEt mixture (9/1 by volume). The filtrate is concentrated to dryness under reduced pressure and the residue is triturated in 400 ml of an n-heptane/ethanol mixture (95/5 by volume), filtered on a glass frit (porosity 3) and dried under reduced pressure to give 35 g of 3-[1-(tetrahydro-pyran-2-yl)-1H-benzimidazol-2-yloxy]benzaldehyde in the form of pale beige crystals (LC/MS-A, tr=1.93 min, MS positive mode m/z=323.16).

C1: Ethyl 8-oxo-9-{3-[1-(tetrahydro-pyran-2-yl)-1H-benzoimidazol-2-yloxy]phenyl}-4,5,6,7,8,9-hexahydro-2H-pyrrolo[3,4-b]quinoline-3-carboxylate

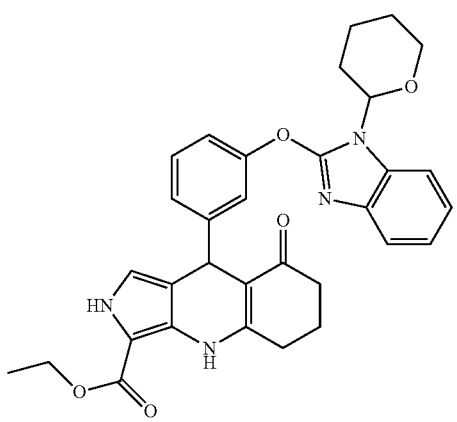 [SMILES: CCOC(=O)c1[nH]cc2c1NC1=C(C(=O)CCC1)C2c1cccc(Oc2nc3ccccc3n2C2CCCCO2)c1]

A 2 l conical flask is charged, with magnetic stirring, with 50 g of 3-amino-2-ethoxycarbonylpyrrole hydrochloride and 0.204 l of 2N sodium hydroxide solution. The mixture is stirred for 15 minutes at ambient temperature (AT), and then extracted with 3×0.3 l of dichloromethane. The organic phases are combined, dried over MgSO$_4$ and concentrated to dryness under reduced pressure. The residue is triturated with n-pentane, filtered and dried under reduced pressure to a constant weight, to give 36.4 g of 3-amino-2-ethoxycarbonylpyrrole in the form of a brown solid.

A 2 l three-necked round-bottomed flask equipped with a stirrer shaft, a thermometer and a condenser is charged with 1.2 l of 1-butanol, 145 g of 3-[1-(tetrahydro-pyran-2-yl)-1H-benzimidazol-2-yloxy]benzaldehyde (0.405 mol, B1), 62.4 g of 3-amino-2-ethoxycarbonylpyrrole (1 eq., 0.405 mol), 46.8 g of 1,3-cyclohexanedione in 97% form (1 eq., 0.405 mol) and 70.5 ml of N,N-diisopropylethylamine (1 eq.) and the mixture is taken to reflux (temperature rise time 55 min, reflux maintained for 30 min, temperature 114° C.) The mixture is then cooled to AT and concentrated to dryness under reduced pressure to give 290 g of a brown oil containing ethyl 8-oxo-9-{3-[1-(tetrahydro-pyran-2-yl)-1H-benzimidazol-2-yloxy]phenyl}-4,5,6,7,8,9-hexahydro-2H-pyrrolo[3,4-b]quinoline-3-carboxylate (LC/MS-A, tr=1.96 min. MS positive mode m/z=553.33). A similar operation carried out with 35 g of 341-(tetrahydro-pyran-[2-yl)-1H-benzimidazol-2-yloxy]-benzaldehyde (0.098 mol, example B1) produces 72 g of a brown oil containing ethyl 8-oxo-9-{3-[1-(tetrahydro-pyran-2-yl)-1H-benzimidazol-2-yloxy]phenyl}-4,5,6,7,8,9-hexahydro-2H-pyrrolo[3,4-b]quinoline-3-carboxylate (LC/MS-A, tr=1.96 min. MS positive mode m/z=553.35).

D1: Ethyl 8-oxo-9-[3-(1H-benzimidazol-2-yloxy) phenyl]-4,5,6,7,8,9-hexahydro-2H-pyrrolo[3,4-b] quinoline-3-carboxylate (compound I)

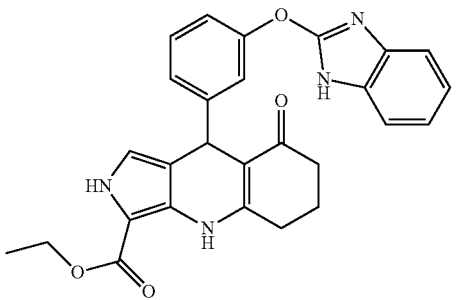 [SMILES: CCOC(=O)c1[nH]cc2c1NC1=C(C(=O)CCC1)C2c1cccc(Oc2nc3ccccc3[nH]2)c1]

A 2 l round-bottomed flask is charged with 224 g of the brown oil containing ethyl 8-oxo-9-{3-[1-(tetrahydro-pyran-2-yl)-1H-benzimidazol-2-yloxy]phenyl}-4,5,6,7,8,9-hexahydro-2H-pyrrolo[3,4-b]quinoline-3-carboxylate (example 1.3), 0.7 l of ethanol and 0.243 l of 2N hydrochloric acid. The mixture is stirred at AT for 16 h and then filtered on a glass frit (porosity 4). The filtrate is concentrated to dryness under reduced pressure and the residue is triturated with 0.5 l of isopropyl ether. The solid obtained is dried under reduced pressure at a constant weight to give 253 g of a brown solid containing ethyl 8-oxo-9-[3-(1H-benzimidazol-2-yloxy) phenyl]-4,5,6,7,8,9-hexahydro-2H-pyrrolo[3,4-b]quinoline-3-carboxylate (LC/MS-A, tr=1.46 min. MS positive mode m/z=469.29). A similar operation carried out with 54 g of the brown oil containing ethyl 8-oxo-9-{3-[1-(tetrahydro-pyran-2-yl)-1H-benzimidazol-2-yloxy]phenyl}-4,5,6,7,8,9-hexahydro-2H-pyrrolo[3,4-b]quinoline-3-carboxylate (C1) produces 60 g of a brown solid containing ethyl 8-oxo-9-[3-(1H-benzimidazol-2-yloxy)phenyl]-4,5,6,7,8,9-hexahydro-2H-pyrrolo[3,4-b]quinoline-3-carboxylate (LC/MS-A, tr=1.48 min. MS positive mode m/z=469.29).

An aliquot fraction of 0.8 g of the product obtained may be purified by chromatography on a 50 g silica cartridge (10-90 µm) (Biotage SNAP, KP-Sil) eluted with an isocratic stage of dichloromethane of 20 min, then a gradient from 0 to 1% by volume of isopropanol in dichloromethane over 1 h, and, finally, an isocratic stage of dichloromethane/isopropanol (99/1 by volume) of 20 min. The fractions containing the expected product are combined to give 0.21 g of a yellow solid. The products of two similar chromatographic separations carried out on the same scale are crystallized from acetonitrile to give a total of 0.16 g of ethyl 8-oxo-9-[3-(1H-benzimidazol-2-yloxy)phenyl]-4,5,6,7,8,9-hexahydro-2H-pyrrolo[3,4-b]quinoline-3-carboxylate in the form of beige crystals (LC/MS-A, tr=1.61 min. MS positive mode m/z=469.28). $^1$H NMR (400 MHz, DMSO-d6): 1.29 (t, J=7.0 Hz, 3H); 1.80 to 1.97 (m, 2H); 2.19 to 2.27 (m, 2H); 2.55 to 2.69 (m, 1H); 2.81 (dt, J=4.8 and 17.2 Hz, 1H); 4.26 (q, J=7.0 Hz, 2H); 5.11 (s, 1H); 6.73 (d, J=3.3 Hz, 1H); 7.02 to 7.16 (m, 5H); 7.25 (t, J=7.9 Hz, 1H); 7.31 to 7.38 (m, 2H); 8.34 (s, 1H); 11.33 (broad s, 1H); 12.26 (broad s, 1H). Elemental analysis: C=68.72%; H=5.10%; N=11.82%; H$_2$O=0.38%.

Example 2

Levogyratory enantiomer (Ia) of ethyl 8-oxo-9-[3- (1H-benzimidazol-2-yloxy)phenyl]-4,5,6,7,8,9- hexahydro-2H-pyrrolo[3,4-b]quinoline-3-carboxylate The levogyratory enantiomer is purified from the crude product of example D1 on a Welk-01RR chiral column, 10 µM, 80×350 mm (Regis. USA) eluted with an n-heptane/dichloromethane/ethanol/triethylamine mixture (50/47.5/2.5/0.1 by volume). The elution of the products is detected by UV spectroscopy at 265 nm. Amounts of 10 g of the crude product described in example D1 are injected in each operation. Under these conditions, the peak corresponding to the levogyratory enantiomer is eluted with a tr of between 50 and 80 min. The fractions of purified levogyratory enantiomer corresponding to the operations needed to purify 310 g of the crude product described in example D1, are combined, homogenized and concentrated to dryness under reduced pressure to give 50 g of a beige solid. Mass spectrum (LC/MS-B): tr=0.77 min; [M+H]+: m/z 469; [M−H]−: m/z 467. $^1$H NMR (400 MHz, DMSO-d6): 1.29 (t, J=7.1 Hz, 3H); 1.79 to 1.97 (m, 2H); 2.19 to 2.27 (m, 2H); 2.55 to 2.66 (m, 1H); 2.81 (dt, J=4.9 and 17.1 Hz, 1H); 4.26 (q, J=7.1 Hz, 2H); 5.12 (s, 1H); 6.73 (d, J=3.4 Hz, 1H); 7.02 to 7.16 (m, 5H); 7.25 (t, J=8.3 Hz, 1H); 7.29 to 7.41 (m, 2H); 8.32 (s, 1H); 11.31 (broad s, 1H); 12.26 (broad s, 1H). IR: principal bands: 1678; 1578; 1525; 1442; 1188; 1043 and 743 cm$^{-1}$. Optical rotation: [α]$_D$=−38.6±0.7 at c=0.698 mg/ml in methanol. Elemental analysis: C=6818%; H=5.92%; N=11.22%; H$_2$O=1.25%.

Example 3

Dextrogyratory enantiomer (Ib) of ethyl 8-oxo-9-[3- (1H-benzimidazol-2-yloxy)phenyl]-4,5,6,7,8,9- hexahydro-2H-pyrrolo[3,4-b]quinoline-3-carboxylate The dextrogyratory enantiomer is obtained by purification of the purified product from example D1 by chromatography on a Welk-01SS chiral column, 10 µM, 60×350 mm (Regis, USA) eluted with an n-heptane/ethanol mixture (7/3 then 6/4 by volume). The elution of the products is detected by UV spectroscopy. The fractions of the dextrogyratory enantiomer are combined, homogenized and concentrated to dryness under reduced pressure to give 1.9 g of a yellow powder. MS (LC/MS-B): tr=077 min; [M+H]+: m/z=469.2; [M−H]−: m/z=467.2. Optical rotation: $[\alpha]_D$=+53.1±1.1 at c=3.6 mg/ml in methanol.

Examples 4-13

The compounds of examples 4-11 were prepared according to the teaching of WO 2007/012972 (see process of claim 26). The tricyclic dihydropyridine products of formula (II) may be prepared according to Scheme II:

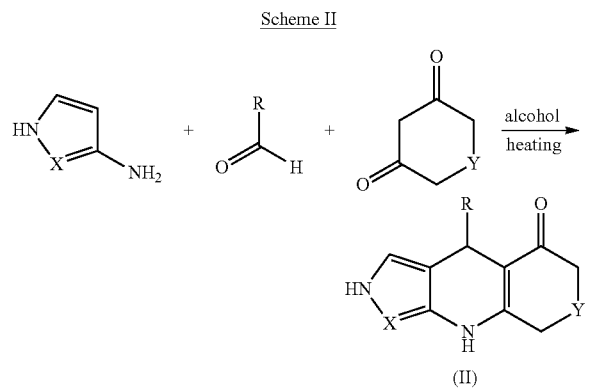

A mixture of one equivalent of pyrazole (X=N) or of pyrrole-2-carboxylate (X=COOEt), one equivalent of aldehyde R—CHO and one equivalent of diketone derivative (Y=CH$_2$, CMe$_2$, N-Boc) is heated at reflux in an alcohol such as ethanol or 1-butanol for a period of between ½ h and several h. The mixture is then cooled to ambient temperature. The desired products are isolated by filtration or else the solvent is evaporated to dryness. If necessary, the crude product is purified by chromatography on silica gel or else by high-performance preparative liquid chromatography (HPLC).

When Y represents N-Boc, the products may be deprotected using a solution of trifluoroacetic acid in dichloromethane (50/50) or else a solution of hydrochloric acid in dioxane (Scheme III):

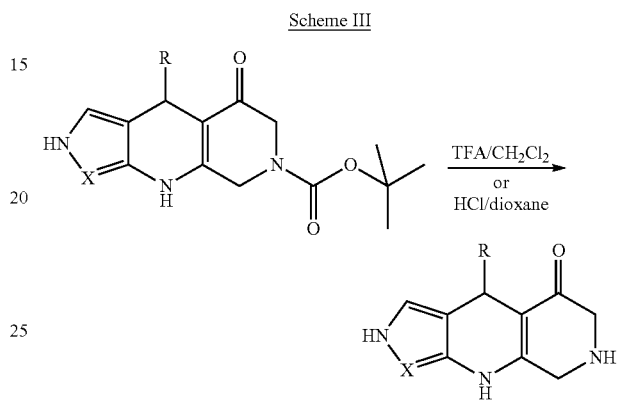

The aldehydes of general formula (III), that are used in the preparation of the compound 4 (R=H), may be obtained according to Scheme IV. R denotes one (n=1) or more substituents (n from 2 to 4) on the benzimidazole nucleus, which are selected from the following: H, F, Cl, Br, OH, SH, CF$_3$, OCF$_3$, OCH$_3$, SCF$_3$, SCH$_3$, OCHF$_2$, OCH$_2$F, SCH$_2$F, (C$_1$-C$_6$)alkyl, O-allyl, phenyl optionally substituted by one or more halogen atoms.

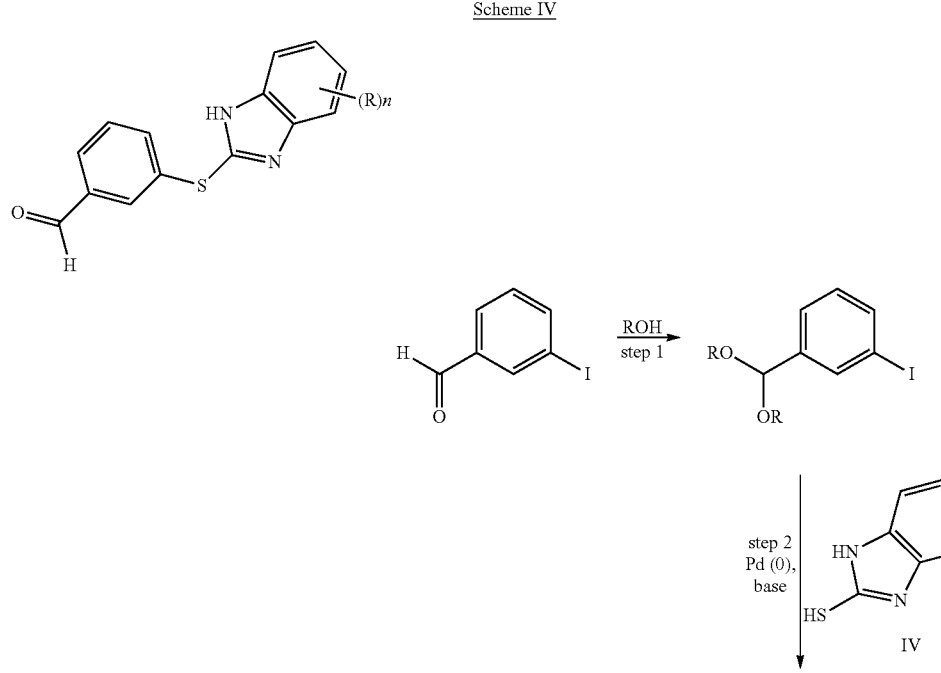

-continued

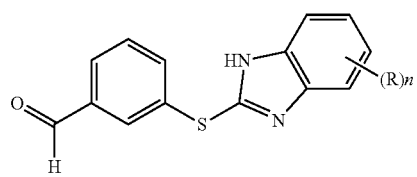

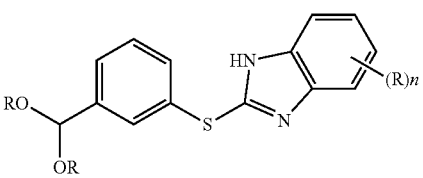

aqueous HCl
step 3

III step 1; the aldehyde function of 3-iodo-benzaldehyde is protected using an alcohol protective group and more particularly a diol protective group (ethylene glycol for example) in the presence of an acid such as para-toluenesulphonic acid in an inert solvent such as toluene and at a temperature of between 20° C. and the boiling temperature of the reaction mixture;

step 2: the intermediate formed is reacted with a product of formula (IV) in the presence of a palladium complex such as bis(dibenzylideneacetone)palladium, a phosphine derivative such as bis[(2-diphenylphosphino)phenyl]ether and a base such as sodium tert-butoxide, in an inert solvent such as toluene and at a temperature of between 20° C. and the boiling temperature of the reaction mixture;

step 3: the aldehyde function is deprotected in the presence of an aqueous acid solution such as hydrochloric acid, optionally in a solvent such as acetone and at a temperature of between 20° C. and the boiling temperature of the reaction mixture.

Table I compares the Aurora A and B inhibition activities, the anti-proliferative activities on the lines HeLa and HCT116, the PDE3 inhibition activity and the metabolism. It is found that compound (I) or (Ia) exhibits a high level of inhibition of Aurora A and B kinases and also very good activity on the lines HeLa and HCT116.

TABLE 1

| Example | Compound | IC50 Aurora B/Incenp [nM] | IC50 Aurora A [nM] | IC50 HeLa [nM] | IC50 HCT116 [nM] | IC50 PDE3 [nM] | Human microsome [%] | Mouse microsome [%] |
|---|---|---|---|---|---|---|---|---|
| 1 - inventive | (I) | 4 | 6 | 205 | nd | 78% inhibition at 1000 nM | 37% | 31% |
| 2 - inventive | Levogyratory compound (Ia) | 1 | 1 | 67 | 20 | 4000 | 32% | 50% |
| 3 - comparative | Dextrogyratory compound (Ib) | 900 | 3800 | >10000 | nd | nd | nd | nd |
| 4 - comparative | | 6 | 72 | 9 664 | nd | nd | 77% | 67% |

TABLE 1-continued

| Example | Compound | IC50 Aurora B/Incenp [nM] | IC50 Aurora A [nM] | IC50 HeLa [nM] | IC50 HCT116 [nM] | IC50 PDE3 [nM] | Human microsome [%] | Mouse microsome [%] |
|---|---|---|---|---|---|---|---|---|
| 5 - comparative | (structure) | 6 | 23 | 9 633 | nd | nd | nd | nd |
| 6 - comparative | (structure) | 13 | 109 | >10000 | nd | nd | nd | nd |
| 7 - comparative | (structure) As the trifluoroacetate | 4 | 3 | 430 | nd | nd | 65% | 96% |
| 8 - comparative | (structure) | 21 | 102 | 6 863 | nd | nd | 80% | 84% |
| 9 - comparative | (structure) | 8 | 15 | 9 462 | nd | nd | nd | nd |

TABLE 1-continued

| Example | Compound | IC50 Aurora B/Incenp [nM] | IC50 Aurora A [nM] | IC50 HeLa [nM] | IC50 HCT116 [nM] | IC50 PDE3 [nM] | Human microsome [%] | Mouse microsome [%] |
|---|---|---|---|---|---|---|---|---|
| 10 - comparative | (structure) | 9 | 22 | 6 692 | nd | nd | nd | nd |
| 11 - comparative | (structure) As the hydrochloride | 107 | 1755 | >10000 | nd | nd | nd | nd |
| 12 - comparative | (structure) Arbitrary configuration dextrogyratory isomer | 3 | 4 | 16 | 1 | 68 | 75% | 81% |
| 13 - comparative | (structure) | 10 | 11 | 20 | nd | 93% inhibition at 1000 nM | 53% | 74% | nd: not determined

TABLE II

| Compound | HCl 0.05N 50/50 water/acetonitrile | NaOH 0.05N 50/50 water/acetonitrile | Phosphate buffer 25 mM pH = 7.4 50/50 water/acetonitrile | Phosphate buffer 25 mM pH = 7.4 + 1% benzylamine 50/50 water/acetonitrile | Phosphate buffer 25 mM pH = 7.4 + 1% 2-mercaptoethanol 50/50 water/acetonitrile |
|---|---|---|---|---|---|
| Compound 12 (comparative) | stable | stable | stable | stable | unstable (half life $t_{1/2}$ = 2.06 h) |
| Compound 2 (levogyratory compound (Ia)) | stable | stable | stable | stable | stable |

TABLE III

| Example | Metabolism measured in the presence of human microsomal fraction | Metabolism measured in the presence of murine microsomal fraction |
|---|---|---|
| Compound 12 (comparative) | 75% | 81% |
| Compound 2 (levogyratory compound (Ia)) | 32% | 50% |

TABLE IV

| Example | Intrinsic clearance measured in the presence of human hepatocytes (in ml.h$^{-1}$.10$^{-6}$ cells) |
|---|---|
| Compound 12 (comparative) | 0.29 average of 3 determinations obtained with 3 different preparations of hepatocytes) |
| Compound 2 (levogyratory compound (Ia)) | 0.121 (average of 5 determinations obtained with 5 different preparations of hepatocytes) |

The invention claimed is:

1. A method of treating cervical or colon cancer in a patient in need thereof comprising administering to said patient a therapeutically effective amount of a pharmaceutical composition comprising a compound of formula

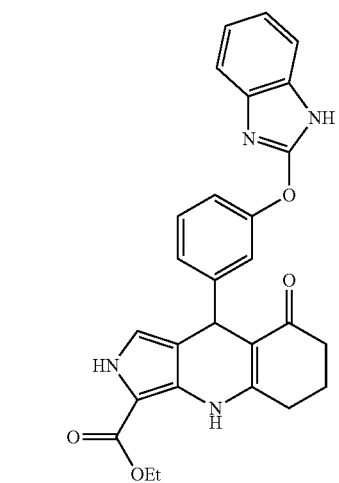

(I)

and at least one pharmaceutically acceptable excipient.

2. The method of claim 1, wherein the compound is in levogyratory form.

3. The method of claim 1, wherein the compound exhibits an optical rotation $[\alpha]_D = -38.6 \pm 0.7$ at a concentration of 0.698 mg/ml in methanol.

4. The method of claim 1, wherein the compound is in the form of a base or addition salt with an acid.

5. The method of claim 4, wherein the compound is a pharmaceutically acceptable acid.

* * * * *